(12) United States Patent
Bernard

(10) Patent No.: US 9,796,663 B2
(45) Date of Patent: Oct. 24, 2017

(54) LACTAME OR AMINO ACID-BASED FATTY AMIDE, AND USE AS AN ORGANOGELATOR

(71) Applicant: Arkema France, Colombes (FR)

(72) Inventor: Michael Y. Bernard, Enghien les Bains (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/906,304

(22) PCT Filed: Jul. 18, 2014

(86) PCT No.: PCT/FR2014/051846
§ 371 (c)(1),
(2) Date: Jan. 20, 2016

(87) PCT Pub. No.: WO2015/011376
PCT Pub. Date: Jan. 29, 2015

(65) Prior Publication Data
US 2016/0168078 A1    Jun. 16, 2016

(30) Foreign Application Priority Data

Jul. 25, 2013 (FR) ..................... 13 57349

(51) Int. Cl.
| | | |
|---|---|---|
| *C07C 223/00* | (2006.01) | |
| *C07C 233/33* | (2006.01) | |
| *A61K 8/42* | (2006.01) | |
| *C08G 69/00* | (2006.01) | |
| *C09J 11/06* | (2006.01) | |
| *A61Q 19/00* | (2006.01) | |
| *C07C 233/31* | (2006.01) | |
| *C09D 4/00* | (2006.01) | |
| *C09D 7/12* | (2006.01) | |

(52) U.S. Cl.
CPC .............. *C07C 233/33* (2013.01); *A61K 8/42* (2013.01); *A61Q 19/00* (2013.01); *C07C 233/31* (2013.01); *C08G 69/00* (2013.01); *C09J 11/06* (2013.01); *A61K 2800/10* (2013.01); *A61K 2800/48* (2013.01); *C09D 4/00* (2013.01); *C09D 7/12* (2013.01)

(58) Field of Classification Search
CPC .................................................... C07C 233/33
USPC ............................................................. 554/35
See application file for complete search history.

(56) References Cited

U.S. PATENT DOCUMENTS

| | | |
|---|---|---|
| 3,969,087 A | 7/1976 | Saito et al. |
| 2009/0223409 A1 | 9/2009 | Banning et al. |
| 2011/0060081 A1 | 3/2011 | Banning et al. |
| 2011/0061565 A1 | 3/2011 | Banning et al. |
| 2011/0061566 A1 | 3/2011 | Banning et al. |
| 2011/0065850 A1 | 3/2011 | Banning et al. |
| 2011/0100254 A1 | 5/2011 | Banning et al. |
| 2012/0129735 A1* | 5/2012 | Dino ........................ C09K 8/36 507/129 |
| 2012/0227622 A1 | 9/2012 | Banning et al. |

FOREIGN PATENT DOCUMENTS

| | | | |
|---|---|---|---|
| JP | 11026573 A | * | 1/1999 |
| JP | 2011026573 A | | 2/2011 |

* cited by examiner

*Primary Examiner* — Deborah D Carr
(74) *Attorney, Agent, or Firm* — Lynn B. Morreale

(57) ABSTRACT

The invention relates to a fatty amide, which is based on:
a) a diamine selected from aromatic or cycloaliphatic or linear $C_2$ to $C_{10}$ aliphatic diamines,
b) a $C_3$ to $C_{12}$ lactam or amino acid,
c) optionally, a second primary diamine different from said diamine a),
d) a hydroxylated fatty monoacid,
e) optionally, a nonhydroxylated monoacid chosen from linear $C_6$ to $C_{12}$ aliphatic acids,
with a mole ratio b/(a+c) of 0.25 to 3/1.
The invention also covers a process for the preparation of said amide and its use as organogelator or rheology additive in an organic solvent medium, in particular in coating, glue or adhesive, mastic, sealant or stripping agent compositions or molding or cosmetic compositions.

16 Claims, No Drawings

LACTAME OR AMINO ACID-BASED FATTY AMIDE, AND USE AS AN ORGANOGELATOR

CROSS-REFERENCE TO RELATED APPLICATIONS

This application is a national stage application under 35 U.S.C. §371 of PCT/FR2014/051846, filed Jul. 18, 2014, which claims benefit to French patent application FR 13.57349, filed Jul. 25, 2013.

The invention relates to an amide of specific composition comprising, in its composition, a lactam or an amino acid in a specific ratio with respect to a diamine, to its process of preparation and to its use as organogelator or rheology additive in various applications, such as coating, mastic, sealant, moulding or cosmetic compositions. These diamides have a performance having a specific behaviour at high temperature, in particular a behaviour of resistance to running at high temperature, preferably at a temperature of at least 60° C. and more particularly at a temperature of at least 70° C.

This is because the amide additive of the present invention has a high temperature stability, making possible, at the same time as the activation of said amide at higher temperatures, its use also in application systems requiring higher temperatures of use. In particular, the diamide of the invention makes possible activation and temperature stability and use at a temperature of at least 60° C.

Moreover, the present invention makes possible, by the use of a specific process practical in its implementation, the fine incorporation of said lactam or amino acid so as to have a well controlled and fine structure of the diamide, as regards its end (fatty) groups, so as to have reproducibility and control of the fine structure and consequently of its rheology performance.

The invention relates first to an amide having a specific composition.

The second subject of the invention is a preparation process with two alternative modes according to mode A) or according to mode B).

Another subject of the invention is an organogelator, in particular rheology additive, which comprises or consists of at least one amide according to the invention.

An organic binder composition which comprises an amide of the invention as organogelator, in particular as rheology additive, the use of said amide for this purpose and the final products thus obtained are also covered.

Thus, the first subject of the present invention is a fatty amide based on (meaning capable of being obtained by reaction of):

a) a primary diamine selected from aromatic, cycloaliphatic or linear $C_2$ to $C_{10}$ aliphatic diamines,
b) a $C_3$ to $C_{12}$ lactam or amino acid, preferably a $C_3$ to $C_{12}$ lactam, more preferably a $C_4$ to $C_9$ lactam and more preferably still a $C_6$ lactam,
c) optionally, a second primary diamine different from said diamine a), preferably chosen from linear $C_2$ to $C_{10}$ aliphatic diamines,
d) a hydroxylated fatty, preferably $C_{18}$ or $C_{20}$, monoacid, more preferably 12-hydroxystearic acid or 14-hydroxyeicosanoic acid, preferably 12-hydroxystearic acid,
e) optionally, a nonhydroxylated monoacid chosen from linear $C_6$ to $C_{12}$, in particular $C_6$ to $C_{10}$, aliphatic acids, with the mole ratio e/d of said monoacid e) with respect to said monoacid d) preferably not exceeding 0.5, and with the mole ratio b/(a+c) ranging from 0.25 to 3/1, preferably from 0.25 to 2/1 and more preferentially from 0.35 to 2/1.

Preferably, in the structure of the amide of the present invention, the possible formation of oligoamide with repeat units derived from the lactam or amino acid b), by chain extension, is limited to a number of said repeat units not exceeding 3, preferably being less than 3 and more particular ranging from 1 to 2.

It should be noted that c), in said mole ratio b/(a+c), is considered only in the case where said diamine c) is present; otherwise, this ratio is reduced to b/a.

According to a specific option of the invention, said fatty amide comprises at least one diamide carrying, at each end, a fatty group based on monoacid d) which can be represented by the formula d-b-a-d, d-b-a-b-d, d-a-d and possibly d-c-d, if said diamine c) is present.

More particularly, when said monoacid e) is present, said amide comprises at least three diamides which can be represented by the formulae d-b-a-d, d-b-a-b-d, e-b-a-d, e-b-a-b-d, e-b-a-e, e-b-a-b-e, d-a-d, d-a-e, e-a-e and possibly e-c-e, d-c-d, d-c-e, if said diamine c) is present.

Mention may be made, as $C_{18}$ or $C_{20}$ monoacid d), of 12-hydroxystearic acid (12-HSA), 9-hydroxystearic acid (9-HSA) and/or 10-hydroxystearic acid (10-HSA) or 14-hydroxyeicosanoic acid (14-HEA) and preferably 12-hydroxystearic acid (12-HSA) and 14-hydroxyeicosanoic acid (14-HEA), 12-hydroxystearic acid (12-HSA) being the most preferred. Said hydroxylated monoacid may be a mixture of at least two of said monoacids d) mentioned.

The diamines a) are primary amines. Mention may be made, as examples of linear aliphatic diamines suitable and preferred for the diamine component a) of said diamide, of ethylenediamine, propylenediamine, butylenediamine (or tetramethylenediamine), pentamethylenediamine or hexamethylenediamine and preferably ethylenediamine or hexamethylenediamine.

Mention may be made, as examples of cycloaliphatic diamines suitable still according to the component a), of cyclohexane-1,3-diamine, cyclohexane-1,4-diamine and cyclohexane-1,2-diamine and in particular cyclohexane-1,3-diamine or cyclohexane-1,4-diamine, isophoronediamine, 1,3-, 1,4- or 1,2-bis(aminomethyl)cyclohexane (derived from the hydrogenation of m-, p- or o-xylylenediamine respectively), preferably 1,3- or 1,4-bis(aminomethyl)cyclohexane, decahydronaphthalenediamine, bis(4-amino-3-methyl-cyclohexyl)methane (BMACM) or bis(4-aminocyclohexyl)methane (BACM), or 1-{[4-(aminomethyl)cyclohexyl]oxy}propan-2-amine. The preferred cycloaliphatic diamines are selected from: cyclohexane-1,3-diamine, cyclohexane-1,4-diamine, 1,3-, 1,4- or 1,2-bis(aminomethyl)cyclohexane, isophoronediamine and bis(4-aminocyclohexyl)methane.

Mention may be made, as suitable and preferred examples of aromatic diamines as component a) of said diamide, of xylylenediamines, preferably m- or p-xylylenediamines, phenylenediamines, preferably m- or p-phenylenediamines, or toluylenediamines, preferably m- or p-toluylenediamines.

Mention may be made, as examples of suitable linear aliphatic diamines preferred for the diamine component c) of said diamide, of ethylenediamine, propylenediamine, butylenediamine (or tetramethylenediamine), pentamethylenediamine, or hexamethylenediamine and preferably ethylenediamine or hexamethylenediamine.

The component b) can be a $C_3$ to $C_{12}$ lactam, that is to say a ring with from 2 to 11 carbon atoms and an amide —$CO_2NH$— group in the ring, where b) can be an equivalent amino acid, form equivalent to the lactam but of linear instead of cyclic structure. The component b) is preferably a lactam, in particular a $C_4$ to $C_9$ lactam and more preferably a $C_6$ lactam, such as caprolactam.

Mention may be made, as examples of monoacids e), of hexanoic, heptanoic, octanoic, nonanoic, decanoic, undecanoic or dodecanoic (or lauric) acid. The following acids are preferred: hexanoic acid, octanoic acid, nonanoic acid and decanoic acid.

Preferably, the mole ratio b/(a+c) between diamines a) and optionally c) and the lactam or amino acid b), in particular lactam b), varies from 0.25 to 2/1 and more preferentially from 0.35 to 2/1.

According to a specific option, said fatty amide according to the invention has, as diamine a), a diamine selected from aromatic diamines and more preferentially, in this case, said diamine a) is an aromatic diamine from: xylylenediamines, preferably m- or p-xylylenediamines, phenylenediamines, preferably m- or p-phenylenediamines, or toluylenediamines, preferably m- or p-toluylenediamines. More particularly, said aromatic diamine a) is a xylylenediamine, preferably m- or p-xylylenediamine and more preferably m-xylylenediamine. Still in this option and according to a more specific case, said hydroxylated monoacid d), that is to say the $C_{18}$ or $C_{20}$ hydroxy acid (or hydroxylated monoacid), is 12-hydroxystearic acid (12-HSA) in the absence of said monoacid e). According to another alternative option, said monoacid d) ($C_{18}$ or $C_{20}$ hydroxy acid) is 12-hydroxystearic acid (12-HSA) in the presence of said monoacid e), preferably e) being selected from hexanoic acid, octanoic acid, nonanoic acid or decanoic acid.

More particularly, said diamine a) and said diamine c), when c) is present, can correspond to, or be in the form of, a mixture of diamines composed of an aromatic diamine a) and of a linear aliphatic diamine c) or to a mixture of a cycloaliphatic diamine a) and of a linear aliphatic diamine c).

Said amide according to the invention can also be defined as the product that may be obtained via a process defined according to mode A) or B) comprising the following successive reaction steps:

according to mode A):
i) reaction of said diamine a) with said lactam or amino acid b), preferably lactam b), with formation of a diamine a) modified with b),
ii) reaction of the product of step i) with said monoacid d) in the presence or absence of said monoacid e) and in the presence or absence of said diamine c), or according to mode B):
i') reaction of said monoacid d) or optionally of said monoacid e), if present, with said lactam or amino acid b), preferably lactam b), with formation of the corresponding monoacid modified with b),
ii') reaction of said modified monoacid (produced) from step i') with said diamine a), in the presence or absence of said diamine c) and if said monoacid from said step i') is said monoacid d), in this case, in the presence or absence of said monoacid e), otherwise, if said monoacid from said step i') is the monoacid e), in this case, in the presence of said monoacid d).

According to a specific option of this definition of the amide of the invention according to mode B), said monoacid e) is present with the successive reaction stages below:
i') reaction of said monoacid e) with said lactam or amino acid b), preferably lactam b), with formation of a monoacid e) modified b),
ii') reaction of the said modified monoacid formed at said stage i') with said diamine a) and said monoacid d) and in the presence or in the absence of said diamine c).

The second subject of the invention is a corresponding process for the preparation of the amide as defined above according to the invention which comprises or is carried out according to at least the mode A) or the mode B) and which comprises the following successive reaction steps as defined above and recalled below.

The process according to mode A) comprises the following successive steps:
i) reaction of said diamine a) with said lactam or amino acid b), preferably lactam b), with formation of a diamine a) modified b),
ii) reaction of the product from stage i) with said monoacid d) in the presence or absence of said monoacid e) and in the presence or absence of said diamine c).

More specifically, in the said process according to the mode A), said component b) is a lactam and said reaction with said amine a) is an anionic oligomerization of said lactam b) using said amine as anionic initiator. This case is particularly valid for a mole ratio b/(a+c)<1.

The process according to mode B) comprises the following successive steps:
i') reaction of said monoacid d) or optionally of said monoacid e), if present, with said lactam or amino acid b), preferably lactam b), with formation of the corresponding monoacid modified with b),
ii') reaction of said modified monoacid (produced) from step i') with said diamine a), in the presence or absence of said diamine c) and if said monoacid from said step i') is said monoacid d), in this case, in the presence or absence of said monoacid e), otherwise, if said monoacid from said step i') is the monoacid e), in this case, in the presence of said monoacid d).

According to a first option of this process, according to mode B), said monoacid e) is present and said process comprises the following successive reaction steps:
i') reaction of said monoacid e) with said lactam or amino acid b), preferably lactam b), with formation of a monoacid e) modified with b),
ii') reaction of said modified monoacid formed in step i') with said diamine a) and said monoacid d) and in the presence or absence of said diamine c).

Another subject of the invention is an organogelator, which comprises or consists of at least one amide as defined above according to the invention or which is obtained by a process as defined above according to the invention. More particularly, it is in preactivated form in an organic solvent, preferably in an organic solvent comprising at least one polar organic solvent.

The invention also covers an organic binder composition, which comprises at least one amide or an organogelator as are defined above according to the invention.

Preferably, this composition is a coating composition, in particular a paint, varnish, ink or gel coat composition, a glue or adhesive composition, a stripping, mastic or sealing composition, a moulding composition or a cosmetic composition.

The invention also covers the use of said amide as organogelator or in particular as rheology additive in an organic solvent medium and more particularly in coating, glue or adhesive, stripping agent, mastic or sealant, moulding or cosmetic compositions.

Finally, the invention covers a finished product which comprises at least one amide as defined according to the invention selected from coatings, mastic or sealant or stripping agent, moulded part or cosmetic, glue or adhesive seal.

The following examples are presented by way of illustration of the invention and of its performance, without any limitation of its coverage.

I—Starting Materials Used

TABLE 1

Starting materials used

| Product | Function | Commercial reference | Supplier |
|---|---|---|---|
| Hexamethylenediamine | diamine c) | Hexamethylenediamine 98% | Aldrich |
| meta-Xylenediamine (m-xylylenediamine) | diamine a) | mXDA | Mitsubishi Chemicals |
| Caprolactam | lactam b) | ε-Caprolactam | Aldrich |
| 12-Hydroxystearic acid | fatty hydroxy acid d) | 12-HSA | Jayant Agro |
| Zinc carboxylate | catalyst | Borchikat ® 22 | OMG Borchers SAS |
| Epoxy resin | binder | Araldite ® GZ 7071X75 | Huntsman |
| Epoxy resin | binder | Araldite ® GY 783 BD | Huntsman |
| Defoamer | defoamer | Byk ® A530 | Byk |
| Dispersing agent | dispersant | Disperbyk ® 110 | Byk |
| titanium dioxide | pigment | Tiona ® 595 | Société des ocres de France |
| Iron oxide | pigment | Bayferrox ® 915 | Lubrizol |
| Zinc phosphate | pigment | ZP 10 | Heucophos |
| Talc | additive | Finntalc ® MO5 | Mondo Minerals |
| Silica | filler | HPF6 | Sibelco |
| n-Butanol | solvent | n-Butanol | Aldrich |
| Polyamide | hardener | Crayamid ® 140 | Arkema |
| Xylene | solvent | Xylene, reagent grade | Aldrich |

II—Methods and Tests Used

The formulations are evaluated with two tests: the flow resistance (or resistance to running) test and an evaluation of the viscosity at different speeds.

Flow Resistance Test

It is carried out using a running tester (Levelling/Sagging Tester from Sheen Instruments) which makes it possible to establish the resistance of a coating to running due to gravity. Manufactured from stainless steel and having a straight blade, this tester comprises notches of increasing values.

The test consists in depositing different strips of paint of parallel thickness on a contrast strip using the running tester. The contrast chart is immediately placed in the vertical position, the thinnest film at the top. The thickness at which the strips meet indicates the tendency towards running.

Evaluation of the Viscosity

It is carried out here using a Brookfield® RV at 25° C. (spindle: S 4). The speed of the spindle is set at 50 RPM (or rpm: rotation per minute) and the viscosity of each paint is measured after it has stabilized. The operation is repeated for a speed of 20 RPM, 10 RPM, 5 RPM or 1 RPM.

III—Preparation and Characterization of the Diamides as Organogelators and Rheology Additives Synthesis of a Meta-(m-)Xylylenediamine/Caprolactam Precondensate According to Said Mode A) According to the Invention 272 g of m-xylylenediamine (i.e., 2 mol of diamine or 4 equivalents of amine Y—NH), 226 g of caprolactam (i.e., 2 mol) and 0.8 g of Borchikat® 22 are introduced, under a nitrogen atmosphere, into a 0.5 liter round-bottomed flask equipped with a thermometer, a Dean and Stark apparatus, a condenser and a stirrer.

The mixture is heated to 250° C. under a stream of nitrogen. The reaction in which the ring is opened by aminolysis is monitored by observing the viscosity. After 8 hours, the viscosity becomes stable and the reaction mixture is cooled to 150° C. and then discharged.

EXAMPLE 1: DIAMIDE BASED ON AN M-XYLYLENEDIAMINE/CAPROLACTAM PRECONDENSATE AND ON HEXAMETHYLENEDIAMINE 64.4 g of m-xylylenediamine/caprolactam precondensate (i.e., 0.25 mol or 0.5 equivalent of amine, the 0.25 mol of precondensate corresponding at the start to 0.25 mol of m-XDA which has reacted with 0.25 mol of caprolactam), 63.8 g of hexamethylenediamine (i.e., 0.25 mol, 0.5 equivalent of amine), and 315.2 g of 12-hydroxystearic acid (1.00 mol, 1.00 equivalent carboxy) are introduced, under a nitrogen atmosphere, into a 1 liter round-bottomed flask equipped with a thermometer, a Dean and Stark apparatus, a condenser and a stirrer.

The mixture is heated to 200° C., still under a stream of nitrogen. The water removed begins to accumulate in the Dean and Stark apparatus from 150° C. The reaction is monitored by the acid and amine numbers. When the acid and amine values are less than 10 mg KOH/g, the reaction mixture is cooled to 150° C. and then discharged into a silicone mould. Once cooled to ambient temperature, the product is micronized mechanically by grinding and sieving in order to obtain a fine and controlled size grading with a mean size obtained of 7μ.

IV—Evaluation of the Rheological Performance in a Paint Formulation

Paint Formulations Used for the Evaluation

1—Preparation

A millbase formulation is prepared with the proportions of Table 3 in the following way:

In a disperser bowl (Dispermill® 2075 yellowline, supplier: Erichsen) heated by a jacket system:

1. Introduction of the epoxy binders and also the dispersant and the defoamer. The homogenization takes place after 2 minutes at 800 revolutions/minute (rpm).
2. Introduction of the fillers and pigments and then grinding at 3000 revolutions/minutes for 30 minutes using a 7 cm blade. By virtue of the jacketed bowl, this stage is cooled with a bath of cold water (20° C.).
3. Introduction of the solvents.

2—Activation 24 hours after the preparation of the millbase, the formulation is again dispersed at 3000 revolutions/minute (rpm) using a 4 cm blade. Each diamide is introduced into the millbase at a given activation temperature (varying from 40° C. to 70° C.) over 20 minutes at 3000 revolutions/minute.

After the addition of the diluted hardener (Table 4) to the millbase, the paints are adjusted with a xylene/butanol (1/1) mixture to 0.4 Pa·s (measured on the cone 4 at 25° C. at 2500 s$^{-1}$ using the Brookfield® CAP 1000). The proportions between the hardener and the mixture of solvents are defined in Table 4.

After the adjustment, the paint is mixed at 1500 revolutions/minute for 2 minutes and then left standing for 30 minutes.

TABLE 2

Millbase formulation

| Composition of the millbase | Function | % by weight |
|---|---|---|
| Araldite ® GZ 7071X75 | binder | 17.3 |
| Araldite ® GY 783 BD | binder | 12.9 |
| Byk ® A530 | defoamer | 0.5 |
| Disperbyk ® 110 | dispersant | 0.5 |
| Tiona ® 595 (titanium dioxide) | pigment | 1.9 |
| Bayferrox ® 915 595 (iron oxide) | pigment | 4.1 |
| ZP 10 (zinc phosphate) | pigment | 7.5 |
| Finntalc ® MO5 | filler | 9.4 |
| Silica HPF6 | filler | 19.0 |
| n-Butanol | solvent | 5.4 |
| Diamide Example 1 | rheology additive | 0.8 |
| TOTAL | | 79.3 |

TABLE 3

Hardener

| Composition of the hardener | % by weight |
|---|---|
| Crayamid ® 140 | 8.8 |
| Xylene | 11.9 |
| TOTAL | 20.7 |

3—Evaluation of the Rheology of the Formulations and Results

A paint formulation was produced following the proportions of Tables 2 and 3 with an activation temperature of 60° C. according to the protocol set out above.

The resistance to running results (Table 4) and the rheology results (Table 5) show that the diamide of Example 1 according to the invention has a thixotropic effect on the formulation once it is activated at 60° C. and a good resistance to running.

TABLE 4

Resistance to running results

| Activation temperature | Diamides | Resistance to running (μ) |
|---|---|---|
| 60° C. | 1 | 375 |

TABLE 5

Rheological results

| Activation temperature | Diamides | Brookfield viscosity at 25° C. (mPa · s) | | | | |
|---|---|---|---|---|---|---|
| | | 1 RPM | 5 RPM | 10 RPM | 50 RPM | 100 RPM |
| 60° C. | 1 | 7800 | 2760 | 1880 | 924 | 736 |

The invention claimed is:

1. A fatty amide derived from the reaction of:
   a) a primary diamine selected from the group consisting of aromatic, cycloaliphatic and linear C2 to C10 aliphatic diamines,
   b) a C3 to C12 lactam or amino acid,
   c) optionally, a second primary diamine different from said diamine a) chosen from the group consisting of linear C2 to C10 aliphatic diamines,
   d) a hydroxylated fatty C18 or C20, monoacid,
   e) optionally, a nonhydroxylated monoacid chosen from the group consisting of linear C6 to C12 aliphatic acids, the mole ratio e/d of said monoacid e) with respect to said monoacid d) not exceeding 0.5,
   and in that the mole ratio b/(a+c) is from 0.25 to 3/1.

2. The fatty amide of claim 1 wherein said monoacid d) is 12 hydroxystearic acid.

3. The fatty amide of claim 1 wherein the mole ratio b/(a+c) is from 0.25 to 2/1.

4. The fatty amide of claim 1 wherein said diamine a) is selected from the group consisting of aromatic diamines.

5. The fatty amide of claim 4 wherein said amine a) is an aromatic diamine selected from the group consisting of: xylylenediamines phenylenediamines, and toluylenediamines.

6. The fatty amide of claim 5 wherein said diamine is xylylenediamine.

7. The fatty amide of claim 4 wherein said monoacid d) is 12 hydroxystearic acid in the absence of said monoacid e).

8. The fatty amide of claim 4 wherein said monoacid d) is 12 hydroxystearic acid in the presence of said monoacid e).

9. A process for the preparation of the fatty amide of claim 1 comprising the successive steps of:
   i) reacting said diamine a) with said lactam or amino acid b), with formation of a diamine a) modified b),
   ii) reacting product from stage i) with said monoacid d) in the presence or absence of said monoacid e) and in the presence or absence of said diamine c).

10. The process according to claim 9, wherein said component b) is a lactam and wherein said reaction with said amine a) is an anionic oligomerization of said lactam b) using said diamine as anionic initiator.

11. A process for the preparation of the fatty amide of claim 1 comprising the successive steps of:
   i') reacting said monoacid d) or optionally of the said monoacid e) if present, with said lactam or amino acid b), to produce corresponding monoacid modified by b),
   ii') reacting said modified monoacid from step i') with said diamine a), in the presence or absence of said diamine c) and if said monoacid from said step i') is said monoacid d), then in the presence or absence of said monoacid e), otherwise, if said monoacid from said step i') is the monoacid e), then in the presence of said monoacid d).

12. The process according to claim 11, wherein said monoacid e) is present with said process comprising successive reaction steps:
- i') reacting said monoacid e) with said lactam or amino acid b), with formation of a monoacid e) modified b),
- ii') reacting said modified monoacid formed at stage i') with said diamine a) and said monoacid d) and in the presence or in the absence of said diamine c).

13. An organogelator comprising or consisting of at least one fatty amide according to claim 1.

14. The organogelator of claim 13 in preactivated form in an organic solvent.

15. An organic binder composition comprising at least one amide according to claim 1.

16. The fatty amide of claim 1, wherein said hydroxylated fatty C18 or C20 monoacid is chosen from the group consisting of 12 hydroxystearic acid and 14 hydroxyeicosanoic acid.

* * * * *